United States Patent [19]
Kauffman

[11] 3,957,778
[45] May 18, 1976

[54] ISOCYANURATE COMPOUNDS AND PREPARATIVE PROCESSES

[75] Inventor: William J. Kauffman, Lititz, Pa.

[73] Assignee: Armstrong Cork Company, Lancaster, Pa.

[22] Filed: Dec. 31, 1974

[21] Appl. No.: 537,689

[52] U.S. Cl. .......................... 260/248 NS; 260/75 N
[51] Int. Cl.² ............................................ C07D 251/34
[58] Field of Search ............................... 260/248 NS

[56] References Cited
UNITED STATES PATENTS

| | | | |
|---|---|---|---|
| 3,235,553 | 2/1966 | Sadle | 260/248 |
| 3,249,607 | 5/1966 | Taub et al. | 260/248 |

*Primary Examiner*—John M. Ford

[57] ABSTRACT

Phenylisocyanurate is reacted with ethyl-chloroacetate in an inert solvent at 25°C. to 150°C. to produce crystalline 1,3-bis(carbethoxymethylene)-5-phenylisocyanurate. The 1,3-bis(carbethoxymethylene)-5-phenylisocyanurate is then heated with a mineral acid to produce crystalline 1,3-bis(carboxymethylene)-5-phenylisocyanurate.

4 Claims, No Drawings

ISOCYANURATE COMPOUNDS AND PREPARATIVE PROCESSES

CROSS-REFERENCE TO RELATED APPLICATIONS

Polyesters derived from 1,3-bis(carboxymethylene)-5-phenylisocyanurate are claimed in copending U.S. patent application entitled Linear Polyesters Containing Isocyanurate Rings and Processes for Preparing Same by William J. Kauffman, Ser. No. 537,688, filed Dec. 31, 1974.

BACKGROUND OF THE INVENTION

1. Field of the Invention

This invention relates to novel isocyanurate organic compounds and processes. More particularly, it relates to 1,3-bis(carboxymethylene)-5-phenylisocyanurate and intermediates thereof. Additionally, it relates to certain processes related to the preparation of the above compounds.

2. Description of the Prior Art

Isocyanurate compositions such as those disclosed in U.S. Pat. No. 3,407,200-Little et al are useful as intermediates in the preparation of amorphous synthetic polymers from which fibers are prepared. These fibers are useful in the manufacture of rope, wearing apparel, and carpeting.

Of particular interest are crystalline isocyanurate compositions which are useful as intermediates in the preparation of crystalline synthetic polymers from which fibers of superior strength and elasticity may be prepared.

It is, therefore, an object of the present invention to provide the novel crystalline isocyanurate compound 1,3-bis(carbethoxymethylene)-5-phenylisocyanurate and its hydrolysis product 1,3-bis(carboxymethylene)-5-phenylisocyanurate.

It is a further object of this invention to provide a process whereby a novel crystalline compound, 1,3-bis(carbethoxymethylene)-5-phenylisocyanurate and its novel crystalline hydrolysis product 1,3-bis(carboxymethylene)-5-phenylisocyanurate.

SUMMARY OF THE INVENTION

In accordance with the present invention, it has now been discovered that 1,3-bis(carboxymethylene)-5-phenylisocyanurate is produced by a process which comprises reacting disodium phenylisocyanurate with ethyl-chloroacetate in an inert solvent to yield crystalline 1,3-bis(carbethoxymethylene)-5-phenylisocyanurate as illustrated by the following reaction:

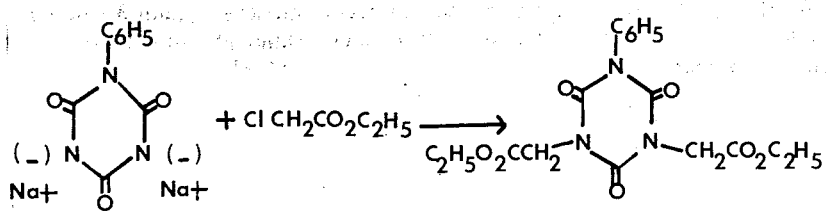

Thereafter, the resultant subject compound is hydrolyzed, by heating the diester compound with aqueous mineral acid, such as hydrochloric acid, or aqueous alkali to the corresponding crystalline 1,3-bis(carboxymethylene)-5-phenylisocyanurate.

Novel polyesters made by condensing 1,3-bis(carboxymethylene)-5-phenylisocyanurate with a polyol such as 1,4-butanediol exhibit excellent strength and high elasticity rendering them useful in the preparation of fibers.

Description of the Preferred Embodiment 1,3-bis(carboxymethylene)-5-phenylisocyanurate is a solid dibasic carboxylic acid, readily obtainable in crystalline form. It is useful in a number of applications, particularly in the preparation of its polymers such as polyesters. Because of its crystalline structure, extremely strong polyester fibers may be prepared which are useful in the production of wearing apparel and carpeting. It is also useful in forming coatings and molded plastic articles.

1,3-(carboxymethylene)-5-phenylisocyanurate can be prepared by the alkylation of a reactive cyanuric acid salt, e.g., an alkali metal salt of cyanuric acid with at least two mole equivalents of ethylchloroacetate in an inert reaction medium to form the diester 1,3-bis(carbethoxymethylene)-5-phenylisocyanurate. The diester is then hydrolyzed as by exposure to a strong mineral acid, such as concentrated hydrochloric acid to form the diacid.

It has been found preferred to employ disodium phenylisocyanurate in the reaction. However, potassium and other salts can be employed with satisfactory results. Workable concentrations of disodium phenylisocyanurate in the reaction mixture will be about 5% to 50% by weight based on the total weight of the reaction mixture.

Any reaction medium which is inert and which will form a suitable reaction mixture at elevated temperatures can be used. For use in the above reaction, the lower dialkyl substituted amides of lower carboxylic acids, such as dimethylformamide, diethylformamide, and dimethylacetamide, are suitable solvents. It is preferred to employ dimethylformamide as the inert reaction medium.

The reaction is carried on at an elevated reaction temperature for a time sufficient to bring satisfactory yields. The ethyl-chloroacetate is added at a reasonable rate to an inert reaction medium containing disodium phenylisocyanurate maintained at a temperature of 25°C. to 150°C., about 70°C. usually being suitable. The reaction will be carried on for a time sufficient to ensure an adequate yield, about two to ten hours being ordinarily ample, depending upon the concentration of the reactants employed, the reaction temperature, and the like.

The 1,3-bis(carbethoxymethylene)-5-phenylisocyanurate is isolated from the reaction mixture by evaporation of the inert reaction medium under reduced pressure. The intermediate compound may be further purified by recrystallization from any suitable solvent such as dimethylformamide, acetonitrile, or carbon tetrachloride.

As mentioned above, the intermediate is convertible to the desired 1,3-bis(carboxymethylene)-5- phenylisocyanurate by acid hydrolysis with, for example, a concentrated mineral acid such as concentrated hydrochloric acid. The hydrolysis can be conveniently effected by heating the hydrolysis mixture of the intermediate at an elevated temperature for a sufficient period of time to convert to the desired 1,3-bis(carboxymethylene)-5-phenylisocyanurate. An hydrolysis time of about one to ten hours at reflux temperature is usually sufficient to bring about the desired hydrolysis with hydrochloric acid. 1,3-bis(carboxymethylene)-5-phenylisocyanurate is recovered and isolated from the hydrolysates by following conventional procedures. Customarily, the diacid is relatively insoluble in most of the mineral acids employed for the hydrolysis, for example, in concentrated hydrochloric acid, and can be recovered from the cooled hydrolysate conveniently by following simple filtration procedures. The 1,3-bis(carboxymethylene)-5-phenylisocyanurate compound can be recrystallized as desired, as from distilled water.

Usable polyesters can be formed by condensing as by heating at elevated temperatures 1,3-bis(carboxymethylene)-5-phenylisocyanurate with the required amounts of a diol having at least two carbon atoms, and preferably from two to ten carbon atoms. Suitable diols may include, for example, 1,4-butanediol, 1,6-hexanediol, ethylene glycol, diethylene glycol, alpha-propylene glycol, and decamethylene glycol. The relative quantities of the 1,3-bis(carboxymethylene)-5-phenylisocyanurate and diol can be varied somewhat to alter average polymer chain links, degree of esterification of the carboxyl groups, and the like. To form a largely linear polymer, at least about one mole of diol is applied for each mole of 1,3-bis(carboxymethylene)-5-phenylisocyanurate.

Polyesters made by condensing 1,3-bis(carboxymethylene)-5-phenylisocyanurate with a polyol as described above exhibit excellent strength and high elasticity rendering them extremely useful in the preparation of fibers for carpets and wearing apparel.

Moreover, 1,3-bis(carboxymethylene)-5-phenylisocyanurate and the fibers derived therefrom are extremely thermally stable, and produce low smoke upon combustion.

The following illustrative examples more fully describe the preparation of the 1,3-bis(carboxymethylene)-5-phenylisocyanurate.

EXAMPLE 1

Preparation of 1,3-bis(carbethoxymethylene)-5-phenylisocyanurate

A quantity of 249 g. (1.0 mole) of disodium phenylisocyanurate is added to 2,000 ml. of dimethylformamide with stirring. Ethyl-chloroacetate (269.6 g., 2.2 mole) is added, and the mixture is heated at 75°C. for eight hours. The dimethylformamide is then removed on a rotary evaporator at reduced pressure, leaving a white solid product. The residue is treated with 2,000 ml. of methylene chloride and washed with water. Evaporation, after drying over sodium sulfate, yields crude 1,3-bis(carbethoxymethylene)-5-phenylisocyanurate. Recrystallization from carbon tetrachloride yields (90%) pure 1,3-bis(carbethoxymethylene)-5-phenylisocyanurate (338 g., 0.9 mole).

Preparation of 1,3-bis(carboxymethylene)-5-phenylisocyanurate 1,3-bis(carbethoxymethylene)-5-phenylisocyanurate (50 g., 0.13 mole) is refluxed (100°C.) with 400 ml. of concentrated hydrochloric acid for eight hours. Upon cooling to 5°C., a solid precipitates from solution. The solid is collected by filtration and is recrystallized from 800 ml. of water to yield (53%) of 1,3-bis(carboxymethylene)-5-phenylisocyanurate (29 g., 0.07 mole).

EXAMPLE 2

Preparation of 1,3-bis(carbethoxymethylene)-5-phenylisocyanurate

In accordance with the procedure of Example 1, a total of 74 g. (0.3 mole) of disodium phenylisocyanurate is added to 800 ml. of dimethylformamide with stirring. Ethyl-chloroacetate (80 g., .65 mole) is added, and the mixture is heated at 70°C. for four hours resulting in a quantitative yield of crude 1,3-bis(carbethoxymethylene)-5-phenylisocyanurate which, upon recrystallization from carbon tetrachloride, yields 80% pure 1,3-bis(carbethoxymethylene)-5-phenylisocyanurate (90 g., 0.24 mole).

Preparation of 1,3-bis(carboxymethylene)-5-phenylisocyanurate

In like fashion, to Example 1, 50 g. (0.13 mole) of 1,3-bis(carbethoxymethylene)-5-phenylisocyanurate is refluxed (100°C.) with 400 ml. of concentrated hydrochloric acid for eight hours. Upon cooling to 5°C., a solid precipitates and is filtered by suction and recrystallized from 800 ml. of water to yield (53%) of 1,3-bis(carboxymethylene)-5-phenylisocyanurate (29 g., .07 mole).

What is claimed is:
1. 1,3-bis(carbethoxymethylene)-5-phenylisocyanurate.
2. 1,3-bis(carbethoxymethylene)-5-phenylisocyanurate.
3. A process for preparing 1,3-bis(carboxymethylene)-5-phenylisocyanurate comprising reacting a salt of phenylisocyanuric acid with ethyl-chloroacetate in an inert reaction medium at a temperature of about 25°C. to 150°C. to form the intermediate 1,3-bis(carbethoxymethylene)-5-phenylisocyanurate and hydrolyzing said intermediate in the presence of an acid to yield 1,3-bis(carboxymethylene)-5-phenylisocyanurate.
4. The process in accordance with claim 3 wherein the inert reaction medium is dimethylformamide.

* * * * *